(12) United States Patent
Preston et al.

(10) Patent No.: US 6,613,892 B2
(45) Date of Patent: *Sep. 2, 2003

(54) HSV VIRAL VECTOR

(75) Inventors: Christopher Maurice Preston, Bearsden (GB); Marion Suzanne Ecob-Prince, Newcastle-upon-Tyne (GB)

(73) Assignee: BTG International Inc., London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/776,774

(22) PCT Filed: Jul. 27, 1995

(86) PCT No.: PCT/GB95/01787
§ 371 (c)(1),
(2), (4) Date: Jan. 28, 1997

(87) PCT Pub. No.: WO96/04394
PCT Pub. Date: Feb. 15, 1996

(65) Prior Publication Data
US 2002/0028925 A1 Mar. 7, 2002

(30) Foreign Application Priority Data
Jul. 29, 1994 (GB) ............................... 9415319

(51) Int. Cl.⁷ ............................... C07H 21/04
(52) U.S. Cl. ............................... 536/23.72; 424/199.1; 424/231.1; 435/69.3; 435/235.1; 435/320.1; 514/44; 530/350; 536/23.1; 536/23.5
(58) Field of Search ............................... 536/23.72, 23.1, 536/23.5; 424/231.1, 199.1; 514/44; 530/350; 435/69.3, 320.1, 235.1

(56) References Cited

U.S. PATENT DOCUMENTS 5,591,639 A * 1/1997 Bebbington

FOREIGN PATENT DOCUMENTS

| GB | WO 91/02788 | 3/1991 |
|----|----|----|
| GB | WO 92/05263 | 4/1992 |
| GB | WO 92/19748 | 11/1992 |
| US | WO 92/07945 | 5/1992 |

OTHER PUBLICATIONS

Ace et al. J Gen Virol vol. 69, 1988, p 2595–2605.*
D.R. Stuart Jamieson et al.; *Quiescent Viral Genomes in Human Fibroblasts After Infection with Herpes Simplex Virus Type 1 Vmw65 Mutants, J. of Gen. Virology* 76:1417–1431 (1995).
M.S. Ecob–Prince et al.; *Expression of β–galactosidase in Neurons of Dorsal Root Ganglia Which Are Latently Infected with Herpes Simplex Virus Type 1, J. of Gen. Virology* 76:1527–1532 (1995).
M.K. Howard et al.; *Transactivation by the Herpes Simplex Virus Virion Protein Vmw65 and viral Permissivity in a Neuronal Cell Line with Reduced Levels of the Cellular Transcription Factor Oct–1, Experimental Cell Research* 207:194–196 (1993).
K.A. Lillycrop et al., *The Octamer Binding Protein Oct–2 Inhibits Transactivation of the Herpes Simplex Virus Immediate–Early Genes by the Virion Protein Vmw65, Virology*196:888–891 (1993).
C.I. Ace et al.; *Construction and Characterization of a Herpes Simplex Virus Type 1 Mutant Unable To Transinduce Immediate–Early Gene Expression, J. of Virology* 63(5):2260–2269 (May 1989).
I. Steiner et al.; *A Herpes Simplex Virus Type 1 Mutant Containing a Nontransinducing Vmw65 Protein Establishes Latent Infection In Viro in the Absence of Viral Replication and Reactivates Efficiently from Explanted Trigeminal Ganglia, J. of Virology* 64(4):1630–1638 (Apr. 1990).
*Nucleic Acids Research*; 20(9) (May 9, 1992).

* cited by examiner

Primary Examiner—James Housel
Assistant Examiner—Ulrike Winkler
(74) Attorney, Agent, or Firm—Alston & Bird LLP (57) ABSTRACT

A recombinant herpes simplex virus (HSV) viral vector genome which has substantially lost its transducing properties as a result of a DNA sequence change in the gene coding for Vmw65 protein and also contains an expressable heterologous gene inserted into a region of the HSV genome which is non-essential for the culture of the virus, the gene being under the control of the immediate early (IE1) gene enhancer of cytomegalovirus (CMV) and to the use of the recombinant HSV genome in therapy and vaccination.

10 Claims, 1 Drawing Sheet

HSV VIRAL VECTOR

The present application is a of 371 of PCT/GB95/01787, international filing date Jul. 27, 1995.

FIELD OF THE INVENTION

The present invention relates to a recombinant herpes simplex virus (HSV), especially type 1 (HSV-1) or type 2 (HSV-2) having a good ability to continuously express an inserted heterologous gene whilst the virus is at the same time maintained in its latent non-replicative state.

BACKGROUND OF THE INVENTION

A distinguishing feature of herpes virus infections is the ability to persist in the host for long periods in a non-replicative or latent state. Herpes simplex virus type 1 (HSV-1) establishes latent infection in human peripheral sensory ganglia and can reactivate to produce recurrent mucocutaneous lesions. Operationally, the pathogenesis of herpes virus infections can be divided into several distinct stages which can be studied individually in experimental animal models: acute viral replication, establishment of latency, maintenance, and reactivation. Following inoculation, HSV-1 replicates at the site of inoculation and is transported to sensory ganglia. Replication at the periphery or in sensory ganglia may increase the amount of virus that can establish latent infection. During latent infection, HSV-1 DNA can be detected in infected tissues but infectious virus cannot be detected. This latent state is often maintained for the life of the host. A variety of stimulae (such as fibrile illness and exposure to ultraviolet irradiation) can interrupt the latent state and cause the reappearance of infectious virus or reactivation.

Transcription of the HSV-1 immediate early (IE) genes is not detectable during latency. However, in tissue culture, IE gene expression is a pre-requisite for viral replication. Transcription of the IE genes is transinduced by a virion protein Vmw65 (transinducing factor) that is a component of the HSV-1 virion. Vmw65 does not bind directly to HSV-1 DNA but mediates transinduction by association with cellular proteins to form a complex which interacts with the IE regulatory element.

Ace et al (1989) report an HSV-1 mutant which contains a 12 bp insertion in the coding region of Vmw65 which is unable to transinduce IE gene expression, though the altered Vmw65 is incorporated into mature virions.

The inventor's previous patent specification WO91/02788 discloses a herpes simplex virus type 1 mutant which includes the mutation within the Vmw65 gene which removes the transinducing properties of the Vmw65 transactivator protein such that the virus remains in its latent state. In addition, a β-galactosidase marker gene under the control of the latency associated transcript (LAT) promoter is inserted into the thymidine kinase (TK) gene and expression of the heterologous gene during latency is observed.

It is an object of the present invention to provide an HSV viral vector having enhanced expression of the inserted heterologous gene during latency.

SUMMARY OF THE INVENTION

Generally speaking, the present invention is based on the discovery that enhanced long term expression during latency may be obtained by use of the IE1 gene enhancer of cytomegalovirus controlling the inserted heterologous gene.

Most specifically, the present invention provides a recombinant herpes simplex virus (HSV) viral vector genome which comprises;

(i) a DNA sequence change in the gene coding for Vmw65 protein such as to substantially remove transinducing properties thereof; and (ii) an expressable heterologous gene inserted into a region of the HSV genome which is non-essential for culture of the virus, the gene being under the control of the immediate early 1 (IE1) gene enhancer of cytomegalovirus (CMV).

DETAILED DESCRIPTION OF THE INVENTION

The Vmw65 sequence change removes the transinducing properties thereof such that expression of HSV IE genes and therefore HSV viral replication in vivo, is substantially removed. The HSV vector is therefore constrained to remain in its latent state. The use of the IE1 CMV enhancer to control the inserted heterologous gene has been found to give excellent long term expression of the heterologous gene during latency. Experiments in mice using the inserted heterologous lacZ gene have showed continuous expression from the latent vector of up to five months. In contrast, use of other promoters such as HSV-1 Vmw110 and Vmw65, and the Moloney murine leukaemia virus enhancer have been found not to give long term expression during latency.

The structure of the human cytomegalovirus (HCMV) enhancer is discussed in Stinski and Roehr (1985). The IE1 enhancer is the promoter-regulatory region upstream of the major immediate early gene of human cytomegalovirus. This enhancer region upstream of the IE1 gene consists of a series of different repeat sequences distributed up to −509 bp from the site for the initiation of transcription. Within this enhancer are a set of inducing sequences. Certain of the sequences within the enhancer region are non-essential and do not effect the level of expression obtained, whilst other sequences promote downstream expression.

The CMV enhancer is generally that derived from human cytomegalovirus (HCMV) and the immediate early 1 (IE1) nomenclature applies particularly to that virus. However, the analogous enhancer from other types of CMV, such as mouse, rat, equine, simian, and guinea pig CMV, may also be employed.

The present invention primarily envisages the use of the entire CMV IE1 enhancer sequence. Indeed in a preferred embodiment of the invention a larger sequence extending to −730 bp and including the entire CMV IE1 enhancer was employed. However, it is clearly within the ambit of the skilled man to modify the naturally occurring enhancer sequence without departing from the general scope of the present invention. Thus, the present invention is concerned not only with the use of the entire CMV IE1 enhancer sequence but also with variations in that sequence, either by insertion, deletion or substitution such that the enhancer properties are not substantially affected.

Other promoter sequences, such as the LAT (latency associated transcript) promoter, may be included upstream of the inserted heterologous gene and HMCV enhancer, but these have not been found to offer any particular advantage according to the present invention.

The position and size of the DNA sequence change in the gene coding for Vmw65 protein is significant, since it is necessary to substantially remove the transinducing properties of the Vmw65 protein (and thereby prevent in vivo replication of the virus and consequent illness of the patient), whilst at the same time retaining the structural properties of the protein required to successfully assemble the complete virion when the virus is cultured. The viral vector of the present invention must be capable of replication under culture conditions so as to be able to produce sufficient quantities of the mutant virus for use, but at the same time the virus should be incapable of replication in vivo. Preferably, the DNA sequence change is achieved by a transition (purine to purine or pyrimidine to pyrimidine) or transversion (purine to pyrimidine or vice versa) alteration of 1–72 base pairs, an oligonucleotide insert of 3–72 base pairs or a deletion of 3–72 base pairs, at a position between amino acids 289 and 480 (especially 289 and 412) of the Vmw65 protein.

The recombinant HSV may be of type HSV-1 or HSV-2 or may be an intertype recombinant between HSV-1 and HSV-2 which comprises nucleotide sequences derived from both types. The recombinant HSV genome will generally be contained in a mutant HSV virus.

HSV has the ability to infect many tissue types and therefore in principle the viral vector of the present invention may be used as a vector directed against a wide variety of cell types. Latency in HSV infection tends to be established within neuronal cells, though it is possible that expressed gene products may translocate from their original point of production. The viral vector of the present invention is thus particularly useful for delivering expressable heterologous genes into neuronal cells. The genes may deliver a therapeutic effect or may deliver an antigenic protein for stimulating the production of antibodies when used as a vaccine. The therapeutic gene is generally a gene associated with a neurological genetic deficiency i.e. it compensates for an inherited or acquired genetic deficiency. Examples of such therapeutic genes include:

(a) human, rat or mouse tyrosine hydroxylase genes 1, 2 or 3, which are relevant to the alleviation of symptoms of Parkinson's disease;

(b) human, rat or mouse nerve growth factor (e.g. the beta subunit) for treatment of Alzheimer's disease and Parkinson's disease;

(c) human, rat or mouse hypoxanthine-guanine phosphoribosyl transferase gene for the treatment of Lesch-Nyhan disease;

(d) human beta-hexosaminidase alpha chain gene, for the treatment of Tay-Sachs and Sandhoff's diseases; and (e) human immunodeficiency virus (HIV) nef gene, for the control of neurological symptoms in HIV-positive individuals.

In particular, the in situ expression of tyrosine hydroxylase by the HSV viral vector of the present invention may help alleviate the symptoms of Parkinson's disease. Tyrosine hydroxylase is a crucial enzyme in the synthesis of dopamine. Deficiency of dopamine is the major cause of symptoms in Parkinson's disease, and current treatment involving the administration of L-dopa gives only—short-lived respite.

The heterologous gene may be inserted into any region of the viral genome which is non-essential for the culture of the virus, i.e. replication of the virus outside the body, particularly in tissue culture. In particular, the insertion of the heterologous gene could be made in the coding sequences or in the flanking control regions of one or more of the following HSV-1 genes:

1. The thymidine kinase gene (the UL23 gene); which is the preferred choice since thymidine kinase is important for pathogenicity of HSV, so that deactivation of its gene may reduce potential pathogenicity of the mutant vector.
2. The RL1 gene
3. The RL2 gene (otherwise named the IE110 gene)
4. The locus encoding the latency associated transcripts
5. The UL2 gene (otherwise named the Uracil-DNA glycosylase gene)
6. The UL3 gene
7. The UL4 gene
8. The UL10 gene
9. The UL11 gene
10. The UL13 gene
11. The UL16 gene
12. The UL20 gene
13. The UL24 gene
14. The UL40 gene (otherwise named the gene encoding the small subunit of ribonucleotide reductase)
15. The UL41 gene (otherwise named the virion host shutoff factor gene)
16. The UL43 gene
17. The UL44 gene
18. The UL45 gene
19. The UL46 gene
20. The UL47 gene
21. The UL50 gene (otherwise named the dUTPase gene)
22. The UL55 gene
23. The UL56 gene
24. The US1 gene (otherwise named the IE68 gene)
25. The US2 gene
26. The US3 gene (otherwise named the protein kinase gene)
27. The US4 gene (otherwise named the glycoprotein G gene)
28. The US5 gene
29. The US7 gene (otherwise named the glycoprotein I gene)
30. The US8 gene (otherwise named the glycoprotein E gene)
31. The US9 gene
32. The US10 gene
33. The US11 gene
34. The US12 gene (otherwise named the IE12 gene)

The UL, US and RL nomenclature system given above is a systematic one, but certain common names of genes are also included.

Another aspect of the present invention relates to the use of the recombinant HSV viral vector genome comprising an appropriate expressible therapeutic gene in the therapy of disease, particularly diseases due to or associated with genetic deficiency. The viral vector may also be used as a vaccine to deliver an antigenic protein.

A further aspect of the present invention relates to a pharmaceutical composition for administering the viral vector comprising the viral vector in admixture with a pharmaceutically acceptable carrier. Generally, the composition will be formulated for parenteral administration—usually by injection—in an appropriate acceptable carrier such as apyrogenic isotonic saline.

The present invention is hereafter further described by way of example only, the insertion of a gene (the lacZ gene coding for β-galactosidase) into the viral vector of the present invention. The lacZ gene is inserted in order to demonstrate the technology, since the presence of the gene is easily detectable. However, for therapeutic or other applications, a heterologous gene would be inserted in an analogous manner; or the lacZ gene could be directly replaced by another heterologous gene.

EXAMPLES SECTION

Materials and Methods

Cells

BHK clone 13 cells (Macpherson and Stoker, 1962) were grown in Eagle's Medium (Glasgow modification) supplemented with 10% newborn calf serum, 10% tryptose phosphate broth, 100 units/ml penicillin and 100 µg/ml streptomycin ($ETC_{10}$).

Viruses

The HSV-1 strain 17 mutant in1814 containing a 12 bp insertion in the coding sequences for Vmw65, and the rescued 'revertant' 1814R, have been described previously (Ace et al, 1989).

To prepare HSV recombinants (summarised in Table 1) containing the *E.coli* lacZ gene inserted within the TK gene, plasmid pMJ27 was first constructed. Plasmid pGX166 (kindly supplied by V. G. Preston) is the cloned HSV-1 strain 17 BamHI p fragment modified by the insertion of an XhoI linker at the SacI site within the TK coding sequences. The HindIII site within the pAT153 vector sequences of pGX166 was destroyed by cleavage, end-filling with Klenow enzyme and religation, to yield pGX166 ΔH3. The *E.coli* lacZ gene plus simian virus 40 (SV40) promoter and enhancer was excised from plasmid FJ3 (Rixon and McLauchlan, 1990) as a 4073 bp BamHI/XbaI fragment and cloned between the BamHI and XbaI sites of pUC18 (previously modified by insertion of an XhoI linker into the SmaI site) to yield pUC18lacZ. The lacZ gene plus SV40 promoter and plyadenylation signals were excised from pUC18lacZ as a SalI/XhoI fragment and cloned into the XhoI site of pGX166 ΔH3. A plasmid in which the direction of lacZ transcription was opposite to that of TK was selected and designated pMJ27. Plasmid pMJ27 contains unique XbaI and HindIII sites flanking the SV40 promoter plus enhancer, and has an unique XhoI site downstream of the SV40 polyadenylation signal.

Figure 1:
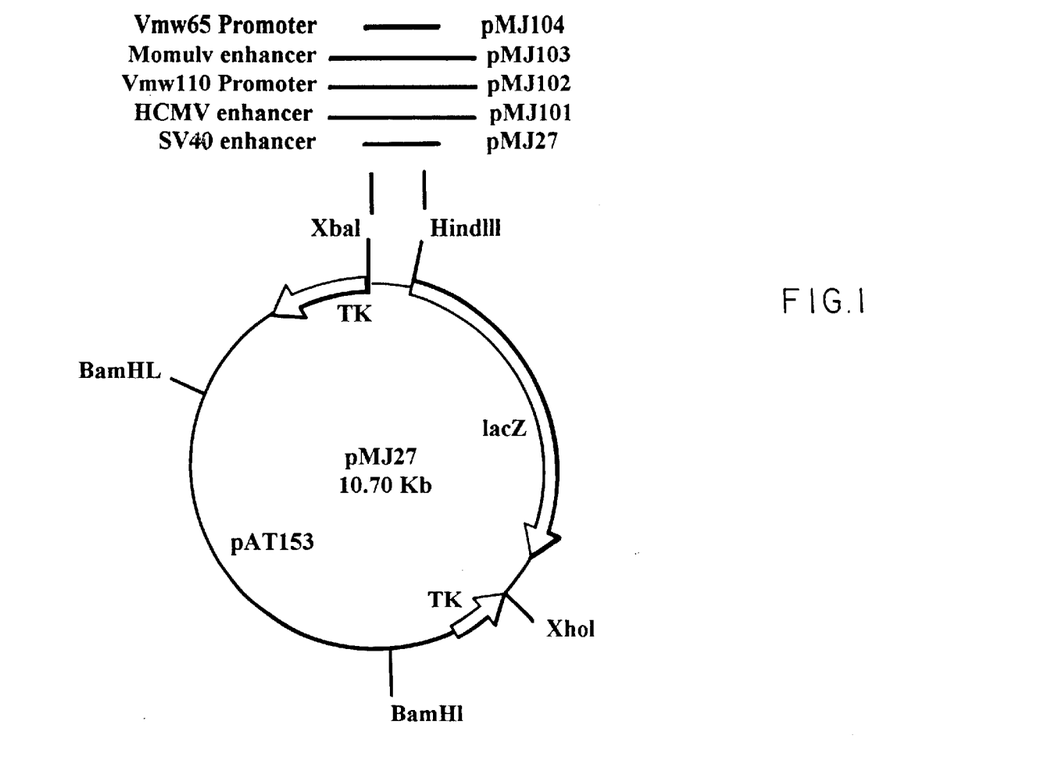
FIG. 1 is a diagrammatic representation of the plasmids used to construct the viruses used in this study. In1853 is a mutant virus according to the present invention, whilst the others are for comparison purposes. Comparison mutants in1863 and in1891 also contain the HCMV enhancer but these are positive for Vmw65 and TK respectively.

The human cytomegalovirus (HCMV) Towne strain enhancer was cloned as a 760 bp Sau3AI fragment (Stinski and Roehr, 1985) from plasmid pHD101-4 (kindly provided by E. Blair) into the BamHI site of pUC18 (from which the SphI site had been inactivated by Klenow treatment and religation), excised as an EcoRI (end-filled)/HindIII fragment and cloned between the XbaI(end-filled) and HindIII sites of pMJ27 in the appropriate orientation, to yield plasmid pMJ101. The HSV-1 Vmw110 promoter was excised as an 836 bp BbvI(end-filled)/SacI fragment from pJR3 (Everett, 1984) and cloned between the SphI (Klenow-treated) and SacI sites of pUC18. The promoter was then removed as an EcoRI(end-filled)/HindIII fragment and cloned between the XbaI(end-filled) and HindIII sites of pMJ27, to yield plasmid pMJ102. The Moloney murine Leukaemia virus (Momulv) promoter plus enhancer was cloned as a 760 bp EcoRI/SmaI fragment, modified by the addition of BamHI linkers at each end (Lang et al, 1983) into the BamHI site of pUC18 (without the SphI site, as described above). The Momulv enhancer was then excised as an EcoRI(end-filled)/HindIII fragment and cloned between the XbaI(end-filled) and HindIII sites of pMJ27 to yield pMJ103. The Vmw65 promoter was excised as a 380 bp TaqI/EcoRV fragment from pMC1 (Campbell et al, 1984) and cloned between the SphI (Klenow treated) and AccI sites of pUC18. The promoter was excised as a XbaI/HindIII fragment and cloned between the XbaI and HindIII sites of pMJ27, to yield pMJ104. The structures of the pMJ plasmids are shown in FIG. 1.

For insertion into the UL43 gene, plasmid p35 (kindly supplied by Dr. C. A. MacLean; MacLean et al, 1991) was modified by insertion of an oligonucleotide linker, providing XbaI and XhoI sites, into the NsiI site within the UL43 coding sequences. Plasmid pMJ101 was partially digested with XbaI, digested with XhoI and the larger fragment spanning the β-gal gene plus HCMV enhancer was cloned between the XbaI and XhoI sites introduced into p35.

Plasmids were cleaved with ScaI and co-transfected into BHK cells with in1814 DNA. Progeny viruses containing lacZ inserts were identified by the development of blue plaques in the presence of 5-bromo-4-chloro-3indolyl-β-D galactopyranoside (X-gal) and purified by three rounds of enrichment for lacZ-containing viruses. Final plaque isolates were grown as small scale cultures and DNA was purified from infected cells. For insertions in the TK gene, DNA was cleaved with EcoRI and analysed by Southern hybridization, using a $^{32}$P radiolabelled 2.4 kbp EcoRI fragment spanning the TK gene as probe. Insertion of lacZ disrupts the 2.4 kbp fragment, yielding species of 1.0 kbp and 2.0 or 5.0 kbp, depending upon the structure of the lacZ-containing plasmid used. Virus isolates showing the correct pattern and lacking detectable hybridization to a 2.4 kbp fragment were grown as stocks.

For insertion into UL43, DNA was cleaved with EcoRI plus BamHI and probed with radiolabelled p35. Insertion of lacZ disrupts the 5.14 kbp EcoRI/BamHI fragment, yielding smaller species. An isolate with the appropriate restriction pattern was grown as a virus stock.

Rescue of the insertion at the Vnw65 locus was achieved by co-transfecting pMC1 with DNA from lacZ-containing viruses. Viral DNA was cleaved with BamHI, probed with pMC1 and isolates lacking a BamHI site within the Vmw65 coding sequences were grown as virus stocks.

Virus titres were determined on BHK cells in the presence of 3 mM hexamethylene bisacetamide (McFarlane et al, 1992).

Inoculation of Mice

Viruses were inoculated subcutaneously into the right rear footpad of 3 to 4 week old male BALB/c mice. Each mouse received 0.025 ml containing approximately $8 \times 10^7$ pfu of virus, diluted in $ETC_{10}$. At various times after inoculation, lumbar dorsal root ganglia (DRG) from spinal levels 2 to 6 (L2 to L6), and feet, were removed by dissection and either used for reactivation studies, stored at −70° for virus assay or fixed in 4% formaldehyde at 4° for 1 h for use in in situ β-gal assay.

β-gal Assays

For quantitative assay of β-gal levels, ganglia were homogenised in phosphate buffered saline (PBS) and cells pelleted by centrifugation. Pellets were resuspended in 50 μl of lysis buffer (10 mM Tris/HCl, pH7.5; 2 mM $MgCl_2$; 10 mM NaCl; 0.1% Nonidet P40), maintained at 4° C. in lysis buffer for 5 min, mixed by vortexing and stored at −70° C. After thawing, 20 μl was assayed in a 100 μl reaction mixture containing 25 mM Tris/HCl, pH7.5; 125 mM NaCl; 2 mM $MgCl_2$; 13 mM β-mercaptoethanol and 0.3 mM 4-methylumbelliferyl-β-D-galactoside. After incubation at 37° for 2 h, 3 μl 20% trichloroacetic acid was added. After 5 min at 4° C., samples were centrifuged at 13,000 g for 5 min. Portions (100 μl) of the supernatant were added to a reagent containing 133 mM glycine and 83 mM $Na_2CO_3$, pH 10.7 and fluorescence measured in a TKO 100 mini-fluorometer (Hoeffer). Protein concentrations of ganglion extracts were determined using a Sigma protein assay kit.

For in situ assay of β-gal, fixed DRG were washed twice with PBS, incubated at 37° C. in a mixture containing 5 mM potassium ferricyanide, 5 mM potassium ferrocyanide, 2 mM $MgCl_2$, 0.02% Nonidet P40, 0.02% sodium deoxycholate and 1 mg/ml X-gal in PBS. Each reaction was performed on a glass slide in a volume of 150 μl, with a 22×40 mm coverslip sealed over the DRG with wax. At 3, 24 or 48h the number or blue cells was counted and the DRG photographed using a Zeiss Axioskop microscope with MC80 camera attachment. Sealed preparations were turned over to check that β-gal containing cells which could not be seen by focusing through the preparation were not missed.

Reactivation

DRG were excised and incubated for 3 days at 37° C. in $ETC_{10}$ plus 10% foetal calf serum and 2.5 μg/ml amphotericin B, conditions previously used to induce reactivation of latent $TK^+$ viruses (Ecob-Prince et al, 1993b; Ecob-Prince and Hassan, 1994). Explanted DRG were then fixed and stained for the presence of β-gal.

Virus Assay

Feet or pooled L3/L4/L5 DRG were homogenized, frozen and thawed twice, and sonicated prior to assay for virus, as described previously (Robertson et al., 1992).

In Situ Hybridization (ISH)

After the in situ assay for β-gal, the fixed explanted DRG from each mouse were embedded together in one block of paraffin, serially-sectioned and the percentage of neurons which expressed LATs was determined by ISH (Ecob-Prince et al, 1993a).

Example 1

Footpad Inoculation of in1853 and in1863

Figure 2:
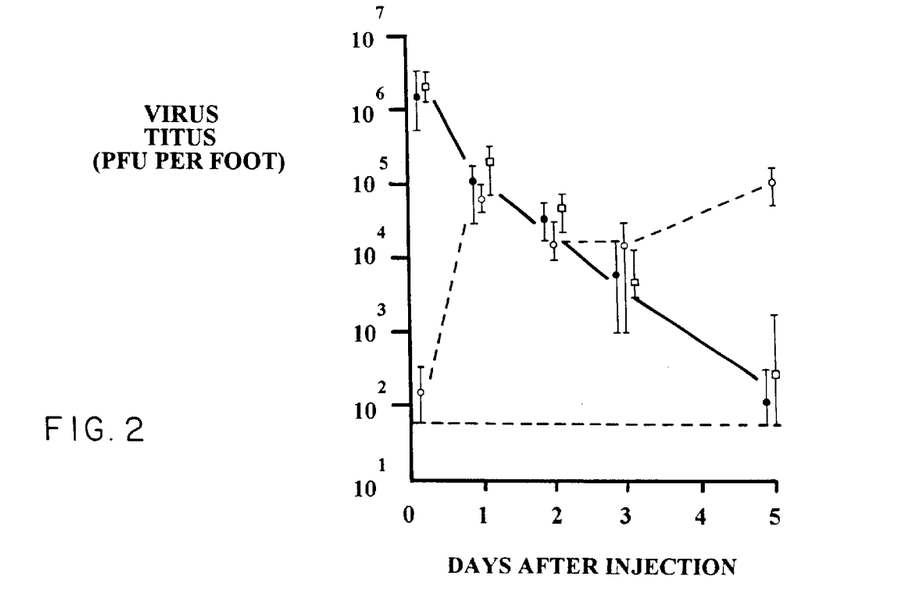
FIG. 2, titres of viruses after injection into mouse footpads. Virus was assayed in extracts of feet after injection of $8 \times 10^7$ pfu of in1853 (□), in1863 (•) or $1 \times 10^5$ pfu of 1814R (○). The means and range of titres from four animals are shown. The level of detection was 50 pfu per foot.

Mutants in1853 and in1863 were injected into mice via the footpad. Their replication in the footpad and within the DRG was measured and β-gal expression was examined in DRG at various times after inoculation. The viruses possessed insertions of the lacZ gene controlled by the HCMV enhancer, at the TK locus, and thus were expected not to replicate in neurons. Injection of in1853 or in1863 at $8 \times 10^7$ pfu resulted in no animal death and only a transient inflammation of the footpad in approximately 10% of mice. High virus titres were observed in the footpad at 2 hr post infection (pi) of either in1853 or in1863 (FIG. 2), but the amount of virus detected decreased over a period of 5 days, suggesting there was a failure to replicate at the periphery and demonstrating that the absence of functional Vmw65 did not affect titres of these $TK^{31}$ viruses in the foot. In contrast, the titres of 1814R following injection at $10^5$ pfu per mouse were maintained within the foot, as described previously (Robertson et al, 1992) When DRG were examined at 5 days post infection (pi), no virus (<5 pfu in total) was detected in pooled L3/L4/L5/L6 ganglia of in1853and in1863-infected mice, whereas virus (90–4200 pfu) was detected in all animals infected with 1814R.

Example 2

Expression of β-gal in DRG Neurons

At various times after inoculation of mice or after explanation of latently-infected ganglia, individual DRG were scored by in situ assay for the number of β-gal containing cells. Invariably, only L3, L4 and L5 ganglia were positive, with the highest number usually in L4. Results are presented in Table 2 as a summation of the values from these ganglia, as suggested by Schmallbruch (1987). In preliminary experiments, DRG from 48 animals were scored after 3 or 21 h incubation in the β-gal reaction mixture, and the number found after 3 h was, on average, 56% of that detected after 21 h. No further increase was observed if the reaction time was extended to 48 h, so counts were thereafter performed following incubation of ganglia for 24 h.

The pattern of β-gal distribution in individual neurons varied, as observed by others (Ho and Mokarski, 1989; Dobson et al., 1990). We recognised a heavy homogenous stain which often extended to the axon of the neuron, a pale homogenous pattern confined to the cell body, a speckled distribution in which 5 to 20 foci of stain were observed in each cell, and a pale-speckled pattern in which the foci were superimposed on a uniformly coloured background. To investigate the relationship between these patterns, DRG were photographed after 3 h or 21 h in β-gal reaction mixture, and changes in the staining pattern of individual neurons observed. Some neurons initially classed as pale became heavy, and some speckled became pale-speckled, but there was little evidence that cells with a speckled pattern at 3 h became homogenously stained by 21 h. The two basic patterns of staining, homogenous and speckled, thus appeared to represent distinct distributions of enzyme rather than be the result of a simple quantitative difference.

The numbers of neurons in DRG infected with in1853 or in1863 which contained β-gal were similar at either 3 or 5 days pi, with the homogenous staining pattern predominating (Table 2). Very few neurons of speckled appearance were detected at 3 days pi, but cells of this type were evident by 5 days. At 1 month pi, when latency was established, the number of β-gal containing neurons had fallen to about half of the value at 3 days pi, and the staining was predominantly speckled (Table 2). However, this predominantly speckled pattern and the number of β-gal containing cells was thereafter stable through 2 and 3 months pi and was also found in DRG at 5 months pi with in1853. These two characteristics of β-gal expression did not appear to be influenced by the presence (in1863) or absence (in1853) of functional Vmw65 in the inoculated virus. The homogenous (usually heavy) pattern was found to predominate during lytic replication (3 and 5 days pi) and reactivation following explantation, whereas the speckled pattern predominated at all times (1, 2, 3 and 5 months pi) during latency.

To investigate whether the long-term detection of β-gal in mice latently-infected with in1853 and in1863 was due to specific features of the HCMV enhancer, additional virus mutants (Table 1) of the same basic design but with different promoters, regulating β-gal expression, in the presence or absence of a nutated Vmw65 gene, were tested. Mutants in1852 and in1862 contain the Momulv enhancer, whereas in1854 and in1864 contained the IE Vmw65 gene promoter. These viruses were injected into mice and β-gal expression examined in DRG at 3 days and 1 month pi, and after 3 months pi either directly or after explanation (Table 3). In addition, LAT-positive neurons were quantified by ISH at 3 months pi (Table 4). All mutants expressed β-gal at 3 days pi, with a preponderance of homogenously stained neurons. The numbers of positive neurons were lower than found after infection with in1853 or in1863, particularly in the case of in1854 and in1864. No significant difference was observed between viruses possessing Vmw65 mutations (in1852 and in1854) and their rescued progeny (in1862 and in1864 respectively). However, no β-gal containing cells were detected during latency after infection with these viruses or with in1855, but explantation resulted in the appearance of 10–20, mainly homogenously stained, neurons. When establishment of latency was assessed by ISH, equivalent number of LAT-expressing neurons were detected at 3 months post injection with all the viruses (Table 4).

To investigate whether persistence of β-gal after infection with in1853 or in1863 was due to the use of the TK gene as an insertion site, mutant in1891 (in which the UL43 gene was chosen as the insertion site) was constructed and tested. Mutants unable to express UL43 are able to establish, maintain and reactivate from latency following injection of mouse pinna (MacLean at el, 1991). At 3 days pi, in1891 caused an apparently more widespread infection of ganglia involving groups of cells stained, thus counting of β-gal containing neurons at 3 days pi was not attempted. Nonetheless, during latency and reactivation, the pattern of β-gal expression was very similar to that observed after injection of in1853 (Table 5). The presence of enzyme was thus a consequence of the use of the HCMV enhancer rather than the site of insertion or the TK⁻ phenotype of in1853 and in1863.

The HCMV enhancer is one of the strongest known promoters, and visualisation of stained ganglia suggested that in1853 and in1863 expressed β-gal to greater extents than the other TK⁻ viruses during acute infection. To quantify enzyme levels, two groups of 9 mice were injected with in1853 or in1855, the most active mutant in lytic infection based on visual observation of β-gal containing cells. At 3 days pi L3, L4 and L5 DRG from the left (uninjected) or right (injected) sides of each of 6 animals were removed by dissection and assayed individually for β-gal levels. The average levels of activity found in DRG of the left side of each group were remarkably similar (Table 6). Compared to these background levels, DRG from mice infected with in1853 were 6.6 times higher, and those from mice infected with in1855 were 1.8 times higher, than background An in situ β-gal assay of DRG from 3 other mice for each virus yielded an average of 122 (for in1853) and 66 (for in1855) stained neurons per mouse, similar to the values obtained previously (Tables 2, 3 and 5), confirming that (even allowing for the difference in numbers of β-gal positive cells) in1853 expressed more β-gal than in1855.

The results present here demonstrate that the presence or absence of functional Vmw65 in the virus did not alter any aspect of heterologous lacZ gene expression or of latency. Viruses which were Vmw65 negative (in1852, in1853 and in1854) could not be distinguished from those which were Vmw65 positive (in1862, in1863 and in1864) in this respect.

Those mutant viruses which contained the HCMV enhancer (in1853, in1863 and in1891) showed good long-term expression of the inserted heterologous lacZ marker gene during latency. However in1863 and in1891 being Vmw65 positive and TK positive respectively are virulent and thus unsuitable for use as a viral vector in vivo.

TABLE 1

Characteristics of the viruses used.

| Virus | Promoter for lacZ | Location of construct | Phenotype * |
|---|---|---|---|
| in1853 | HCMV | TK | TK⁻/Vmw65⁻ |
| in1863 | HCMV | TK | TK⁻/Vmw65⁺ |
| in1852 | Momulv | TK | TK⁻/Vmw65⁻ |
| in1862 | Momulv | TK | TK⁻/Vmw65⁺ |
| in1854 | Vmw110 | TK | TK⁻/Vmw65⁻ |
| in1864 | Vmw110 | TK | TK⁻/Vmw65⁺ |
| in1855 | Vmw65 | TK | TK⁻/Vmw65⁻ |
| in1891 | HCMV | UL43 | TK⁺/Vmw65⁻ |

* Vmw65⁻ and Vmw65⁺ refer to transactivating activity.

TABLE 2

The proportions of cells positive for B-gal which have different patterns of staining at different times after infection of explantation of the DRG.

| Time after infection or explantation | Total* (L3, 4, 5) | Heavy | Pale | Speckled | Pale/ Speckled |
|---|---|---|---|---|---|
| in1853: 3 dpi | 103 | 82 (79%) | 10 (9%) | 8 (8%) | 3 (3%) |
| 5 dpi | 88 | 21 (24%) | 36 (41%) | 22 (25%) | 9 (10%) |
| 1 mpi | 37 | 3 (8%) | 3 (7%) | 27 (74%) | 4 (11%) |
| 2 mpi | 65 | 9 (14%) | 16 (25%) | 28 (43%) | 12 (18%) |
| 3 mpi | 49 | 3 (6%) | 2 (4%) | 38 (78%) | 6 (12%) |
| 5 mpi | 66 | 1 (1%) | 0 | 55 (86%) | 10 (13%) |
| 3 dpe | 78 | 29 (37%) | 32 (40%) | 14 (18%) | 4 (5%) |
| in1863: 3 dpi | 70 | 44 (63%) | 10 (14%) | 12 (17%) | 4 (6%) |
| 5 dpi | 65 | 12 (18%) | 25 (39%) | 22 (33%) | 6 (10%) |
| 1 mpi | 49 | 3 (7%) | 1 (3%) | 40 (82%) | 4 (8%) |
| 2 mpi | 51 | 2 (4%) | 4 (6%) | 43 (84%) | 3 (6%) |
| 3 mpi | 57 | 3 (6%) | 6 (10%) | 37 (65%) | 11 (19%) |
| 3 dpe | 78 | 28 (36%) | 31 (40%) | 16 (20%) | 3 (4%) |

*all values are an average of at least 3 animals at each time
dpi, days post infection
mpi, months post infection (latent virus)
dpe, days post explantation (reactivating virus)

TABLE 3

The proportions of cells positive for b-gal which show diferent patterns of staining at different times after infection or explantation of the DRG infected with viruses containing lacZ controlled by different promoters in the TK gene location.

| Time after infection or explantation | Total* (L3, 4, 5) | Heavy | Pale | Speckled | Pale/ speckled |
|---|---|---|---|---|---|
| 3 dpi: in1862 | 41 | 9 (22%) | 23 (56%) | 8 (20%) | 1 (2%) |
| in1852 | 57 | 9 (15%) | 33 (58%) | 12 (21%) | 3 (6%) |
| in1864 | 18 | 5 (25%) | 13 (75%) | zero | zero |
| in1854 | 22 | 6 (27%) | 16 (73%) | zero | zero |
| in1855 | 77 | 22 (28%) | 54 (70%) | 1 (2%) | zero |
| 1 mpi All viruses | zero | zero | zero | zero | zero |
| 3 mpi All viruses | zero | zero | zero | zero | zero |
| 3 dpe in1862 | 11 | 1 (9%) | 10 (91%) | zero | zero |
| in1852 | 12 | 3 (25%) | 7 (50%) | 1 (8%) | 1 (9%) |
| in1864 | 10 | 2 (20%) | 7 (70%) | 1 (10%) | zero |

TABLE 3-continued

The proportions of cells positive for b-gal which show diferent patterns of staining at different times after infection or explantation of the DRG infected with viruses containing lacZ controlled by different promoters in the TK gene location.

| Time after infection or explantation | Total* (L3, 4, 5) | Heavy | Pale | Speckled | Pale/ speckled |
|---|---|---|---|---|---|
| in1854 | 16 | 4 (25%) | 12 (75%) | zero | zero |
| in1855 | 17 | 2 (12%) | 15 (88%) | zero | zero |

*values are the average of 3 mice (3 dpi, 1 mpi) or 2 mice (3 mpi, 3 dpe)

TABLE 4

A comparison of the total number of neurons in L3, L4 and L5 DRG which contained either β-gal or LATs at 3 months pi.

| Virus | β-gal positive neurons | LAT-positive neurons |
|---|---|---|
| in1862 | 0 | 192 |
| in1852 | 0 | 161 |
| in1864 | 0 | 117 |
| in1854 | 0 | 155 |
| in1853 | 49 | 143 |
| in1863 | 57 | 218 |
| in1891 | 32 | 172 |
| in1855 | 0 | 224 |

TABLE 5

The proportions of cells positive for β-gal which showed different patterns of staining at different times after infection or following explantation of the DRG infected with viruses containing HCMV-lacZ in different locations.

| Time after infection or explantation | Total (L3, 4, 5) | Heavy | Pale | Speckled | Pale/ speckled |
|---|---|---|---|---|---|
| in1853: 3 dpi | 110* | 35 (32%) | 65 (59%) | 9 (8%) | 1 (1%) |
| 1 mpi | 23* | zero | 1 (3%) | 17 (77%) | 5 (20%) |
| 3 mpi | 43† | zero | 3 (8%) | 38 (89%) | 2 (3%) |
| 3 dpe | 75† | 30 (40%) | 32 (42%) | 8 (10%) | 6 (8%) |
| in1891 1 mpi | 15* | <1 (4%) | 3 (19%) | 10 (69%) | 1 (8%) |
| 3 mpi | 32† | zero | 4 (13%) | 21 (65%) | 7 (22%) |
| 3 dpe | 67† | 29 (42%) | 30 (44%) | 8 (13%) | zero |

*average value for 3 mice (9DRG) per time point
†average value for 2 mice (6DRG) per time point

TABLE 6

Assay for β-gal in DRG 3 days pi with different virus constructs.

| Virus | Animal no. | Units of β-gal per μg protein | | Right/Left |
|---|---|---|---|---|
| | | Left* | Right* | |
| in1853 | 1. | 191 | 1562 | 7.7 |
| | 2. | 325 | 1767 | 5.4 |
| | 3. | 350 | 2828 | 8.1 |
| | 4. | 196 | 1161 | 5.9 |
| | 5. | 219 | 1238 | 5.7 |
| | 6. | 126 | 858 | 6.8 |
| | average | 235 | 1569# | 6.6 |
| in1855 | 7. | 212 | 322 | 1.5 |
| | 8. | 426 | 869 | 2.0 |
| | 9. | 445 | 653 | 1.5 |
| | 10. | 157 | 223 | 1.4 |
| | 11. | 107 | 307 | 2.9 |
| | 12. | 119 | 174 | 1.5 |
| | average | 244 | 425## | 1.8 |

*pooled values of L3 + L4 + L5 DRG
right significantly > left, p < 0.01
right significantly > left, p < 0.05

References

ACE, C. I., DALRYMPLE, M. A., RAMSAY, F. H., PRESTON, V. G. and PRESTON, C. M. (1988). Mutational analysis of the herpes simplex virus type 1 trans-inducing factor Vmw65. J. Gen. Virol. 69, 2595–2605.

ACE, C. I., McKEE, T. A., RYAN, J. M., CAMERON, J. M. and PRESTON, C. M. (1989). Construction and characterization of a herpes simplex virus type 1 mutant unable to transinduce immediate-early gene expression. J. Virol. 63, 2260–2269.

ANDERSON, J. K., GARBER, D. A., MEANEY, C. A. and BREAKEFIELD, X. O. (1992). Gene transfer into mammalian central nervous system using herpes virus vectors: extended expression of bacterial lacZ in neurons using the neuron-specific enolase promoter. Human Gene Therapy 3, 487–499.

CAMPBELL, M. E. M., PALFREYMAN, J. W. and PRESTON, C. M. (1984). Identification of herpes simplex virus DNA sequences which encode a trans-acting polypeptide responsible for stimulation of immediate early transcription. J. Mol. Biol. 180, 1–19.

CHIOCCA, E. A., CHOI, B. B., CAI, W., DELUCA, N. A., SCHAFFER, P. A., DIFIGLIA, M., BREAKEFIELD, X. O. and MARTUZA, R. L. (1990). Transfer and expression of the lacZ gene in rat brain neurons mediated by herpes simplex virus mutants. New Biologist 2, 739–746.

COEN, D. M., KOSZ-VNENCHAK, M., JACOBSON, J. G., LEIB, D. A., BOGARD, C. L., SCHAFFER, P. A., TYLER, K. L. and KNIPE, D. M. (1989). Thymidine kinase-negative herpes simplex virus mutants establish latency in mouse trigeminal ganglia but do not reactivate. Proc. Natl. Acad. Sci. USA 86, 4736–4740.

CROEN, K. D., OSTROVE, J. M., DRAGOVIC, L. J. and STRAUS, S. E. (1987). Latent herpes simplex virus in human trigeminal ganglia: detection of an immediate-early gene 'antisense' transcript by in situ hybridization. New Engl. J. Med. 317, 1427–1432.

DOBSON, A. T., MARGOLIS, T. P., SEDARATI, F., STEVENS, J. G. and FELDMAN, L. T. (1990). A latent, nonpathogenic HSV-1-derived vector stably expresses β-galactosidase in mouse neurons. Neuron 5, 353–360.

DOBSON, A. T., SEDARATI, F., DEVI-RAO, G., FLANAGAN, W. M., FARRELL, M. J., STEVENS, J. G., WAGNER, E. K. and FELDMAN, L. T. (1989). Identification of the latency-associated transcript promoter by expression of rabbit beta-globin mRNA in mouse sensory nerve ganglia latently infected with a recombinant herpes simplex virus. J. Virol. 63, 3844–3851.

ECOB-PRINCE, M. S. and HASSAN, K. (1994). Reactivation of latent herpes simplex virus from explanted dorsal root ganglia. J. Gen. Virol. 75, in press.

ECOB-PRINCE, M. S., PRESTON, C. M., RIXON, F. J., HASSAN, K. and KENNEDY, P. G. E. (1993a). Neurons containing latency-associated transcripts are numerous and widespread in dorsal root ganglia following footpad inoculation of mice with herpes simplex virus type 1 mutant in1814. J. Gen. Virol. 74, 985–994.

ECOB-PRINCE, M. S., RIXON, F. J., PRESTON, C. M., HASSAN, K. and KENNEDY, P. G. E. (1993b). Reactivation in vivo and in vitro of herpes simplex virus from mouse dorsal root ganglia which contain different levels of latency-associated transcripts. J. Gen. Virol. 74, 995–1002.

EFSTATHIOU, S., KEMP, S., DARBY, G. K. and MINSON, A. C. (1989). The role of herpes simplex virus type 1 thymidine kinase in pathogenesis. J. Gen. Virol. 70, 869–879.

EVERETT, R. D. (1984). Transactivation of transcription by herpes virus products: Requirement for two HSV-1 immediate-early polypeptides for maximum activity. EMBO J. 3, 3135–3141.

EVERET, R. D. (1987). The regulation of transcription of viral and cellular genes by herpesvirus immediate-early gene products. Anticancer Res. 7, 589–604.

EVERETT, R. D. (1989). Construction and characterisation of herpes simplex virus type 1 mutants with defined lesions in immediate early gene 1. J. Gen. Virol. 70, 1185–1202.

FINK, D. J., STERNBERG, L. R., WEBER, P. C., MATA, M., GOINS, W. F. and GLORIOSO, J. C. (1992). IN vivo expression of β-galactosidase in hippocampal neurons by HSV-mediated gene transfer. Human Gene Therapy 3, 11–19.

FRASER, N. W., BLOCK, T. M. and SPIVACK, J. G. (1992). The latency-associated transcripts of herpes simplex virus: RNA in search of a function. Virology 191, 1–8.

GOINS, W. F., STERNBERG, L. R., CROEN, K. D., KRAUSE, P. R., HENDRICKS, R. L., FINK, D. J., STRAUS, S. E., LEVINE, M. and GLORIOSO, J. C. (1994). A novel latency-active promoter is contained within the herpes simplex virus type 1 UL flanking repeats. J. Virol. 68, 2239–2252.

HALL, L. M., DRAPER, K. G., FRINK, R. J., COSTA, R. H. and WAGNER, E. K. (1982). Herpes simplex virus mRNA species mapping in EcoRI fragment I. J. Virol. 43, 594–607.

HARRIS, R. A. and PRESTON, C. M. (1991). Establishment of latency in vitro by the herpes simplex virus type 1 mutant in 1814. J. Gen. Virol. 72, 907–913.

HO, D. Y. and MOCARSKI, E. S. (1989). Herpes simplex virus latent RNA (LAT) is not required for latent infection in the mouse. Proc. Natl. Acad. Sci. USA 86, 7596–7600.

HONESS, R. W. and ROIZMAN, B. (1974). Regulation of herpesvirus macromolecular synthesis. I. Cascade regulation of the synthesis of three groups of viral proteins. J. Virol. 14, 8–19.

JACOBSON, J. G., RUFFNER, K. L., KOSZVNENCHAK, M., HWANG, C. B., WOBBE, K. K., KNIPE, D. M. and COEN, D. M. (1993). Herpes simplex virus thymidine kinase and specific stages of latency in murine trigeminal ganglia. J. Virol. 67, 6903–6908.

KATAN, M., HAIGH, A., VERRIJZER, P. C., VAN DER VLIET, P. C. and O'HARE, P. (1990). Characterization of a cellular factor which interacts functionally with oct-1 in the assembly of a multicomponent transcription complex. Nucleic Acids Res. 18, 6871–6880.

KATZ, J. P., BODIN, E. T. and COEN, D. M. (1990). Quantitative polymerase chain reaction analysis of herpes simplex virus DNA in ganglia of mice infected with replication-incompetent mutants. J. Virol. 64, 4288–4295.

KEMP, L. M., DENT, C. L. and LATCHMAN, D. S. (1990). Octamer motif mediates transcriptional repression of HSV immediate-early genes and octamer-containing cellular promoters in neuronal cells. Neuron 4, 215–222.

KRISTIE, T. M. and ROIZMAN, B. (1988). Differentiation and DNA contact points of the host proteins binding at the cis site for virion-mediated induction of herpes simplex virus 1 α genes. J. Virol. 62, 1145–1157.

LANG, J. C., WILKIE, N. M. and SPANDIDOS, D. A. (1983). Characterization of cukaryotic transcriptional control signals by assay of herpes simplex virus type 1 thymidine kinase. J. Gen. Virol. 64, 2679–2696.

LEIST, T. P., SANDRI-GOLDIN, R. M. and STEVENS, J. G. (1989). Latent infections in spinal ganglia with thymidine kinase-deficient herpes simplex virus. J. Virol. 63, 4976–4978.

LILLYCROP, K. A. and LATCHMAN, D. S. (1992). Alternative splicing of the oct-2 transcription factor RNA is differentially regulated in neuronal cells and B cells and results in protein isoforms with opposite effects on the activity of octamer/TAATGARAT-containing promoters. J. Biol. Chem. 267, 24960–24965.

LILLYCROP, K. A., DENT, C. L., WHEATLEY, S. C., BEECH, N. M., NINKINA, N. N., WOOD, J. N. and LATCHMAN, D. S. (1991). The octamer-binding protein oct-2 represses HSV immediate-early genes in cell lines derived from latently infectable sensory neurons. Neuron 7, 381–390.

LILLYCROP, K. A., HOWARD, M. K., ESTRIDGE, J. K. and LATCHMAN, D. S. (1994). Inhibition of herpes simplex virus infection by ectopic expression of neuronal splice variants of the oct-2 transcription factor. Nucleic Acids Res. 22, 815–820.

McFARLANE, M., DAKSIS, J. I. and PRESTON, C. M. (1992). Hexamethylene bisacetamide stimulates herpes simplex virus immediate early gene expression in the absence of trans-induction by Vmw65. J. Gen. Virol. 73, 285–292.

McKNIGHT, J. L. C., KRISTIE, T. M. and ROIZMAN, B. (1987). Binding of the virion protein mediating α gene induction in herpes simplex virus 1-infected cells to its cis site requires cellular proteins. Proc. Natl. Acad. Sci. USA 84, 7061–7065.

McLENNAN, J. L. and DARBY, G. (1980). Herpes simplex virus latency: the cellular location of virus in dorsal root ganglia and the fate of the infected cell following virus activation. J. Gen. Virol. 51, 233–243.

MACKEM, S. and ROIZMAN, B. (1982). Structural features of the α gene 4, 0, and 27 promoter-regulatory sequences which confer α regulation on chimeric thymidine kinase genes. J. Virol. 44, 939–949.

MACLEAN, C. A., EFSTATHIOU, S., ELLIOTT, M. L., JAMIESON, F. E. and McGEOCH, D. J. (1991). Investigation of herpes simplex virus type 1 genes encoding multiply inserted membrane proteins. J. Gen. Virol. 72, 897–906.

MACPHERSON, I. and STOKER, M. (1962). Polyoma transformation of hamster cell clones—an investigation of genetic factors affecting cell competence. Virology 16, 147–151.

MARGOLIS, T. P., BLOOM, D. C., DOBSON, A. T., FELDMAN, L. T. and STEVENS, J. G. (1993). Decreased reporter gene expression during latent infection with HSV LAT promoter constructs. Virology 197, 585–592.

O'HARE, P. and GODING, C. R. (1988). Herpes simplex virus regulatory elements and the immunoglobulin octamer domain bind a common factor and are both targets for virion transactivation. Cell 54, 435–445.

POST, L. E., MACKEM, S. and ROIZMAN, B. (1981). Regulation of α genes of herpes simplex virus: Expression of chimeric genes produced by fusion of thymidine kinase with α gene promoters. Cell 24, 555–565.

PRESTON, C. M. (1979). Control of herpes simplex virus type 1 mRNA synthesis in cells infected with wild type virus or the temperature sensitive mutant tsK. J. Virol. 29, 275–284.

PRESTON, C. M., FRAME, M. C. and CAMPBELL, M. E. M. (1988). A complex formed between cell components and an HSV structural polypeptide binds to a viral immediate early gene regulatory sequence. Cell 52, 425–434.

RIXON, F. J. and McLAUCHLAN, J. (1990). Insertion of DNA sequences at a unique restriction enzyme site engineered for vector purposes into the genome of herpes simplex virus type 1. J. Gen. Virol. 71, 2931–2939.

ROBERTSON, L. M., MACLEAN, A. R. and BROWN, S. M. (1992). Peripheral replication and latency reactivation kinetics of the non-neurovirulent herpes simplex virus type 1 variant 1716. J. Gen. Virol. 73, 967–970.

ROCK, D., LOCKENSGARD, J., LEWIS, T. and KUTISH, G. (1992). Characterization of dexamethasone-induced reactivation of latent bovine herpesvirus 1. J. Virol. 66, 2484–2490.

ROIZMAN, B. and SEARS, A. E. (1987). An inquiry into the mechanisms of herpes simplex virus latency. Ann. Rev. Microbiol. 41, 543–571.

SACKS, W. R. and SCHAFFER, P. A. (1987). Deletion mutants in the gene encoding the herpes simplex virus type 1 immediate-early protein ICP0 exhibit impaired growth in culture. J. Virol. 61, 829–839.

SACKS, W. R., GREENE, C. C., ASCHMAN, D. P. and SCHAFFER, P. A. (1985). Herpes simplex virus type 1 ICP37 is an essential regulatory protein. J. Virol. 55, 796–805.

SADOWSKI, I., M A, J., TRIEZENBERG, S. J. and PTASHNE, M. (1988). GAL4-VP16 is an unusually potent transcriptional activator. Nature 335, 563–564.

SANDRI-GOLDIN, R. M. and MENDOZA, G. E. (1992). A herpesvirus regulatory protein appears to act post-transcriptionally by affecting mRNA processing. Genes Dev. 6, 848–863.

SAWTELL, N. M. and THOMPSON, R. L. (1992). Rapid in vivo reactivation of herpes simplex virus in latently infected murine ganglionic neurons after transient hyperthermia. J. Virol. 66, 2150–2156.

SCHMALBRUCH, H. (1987). Loss of sensory neurons after sciatic nerve section in the rat. Anatomical Record 219, 323–329.

SEARS, A. E., HUKKANEN, V., LABOW, M. A., LEVINE, A. J. and ROIZMAN, B. (1991). Expression of herpes simplex virus 1 α transinducing factor (VP16) does not induce reactivation of latent virus or prevent the establishment of latency in mice. J. Virol. 65, 2929–2935.

SEDARATI, F., MARGOLIS, T. P. and STEVENS, J. G. (1993). Latent infection can be established with drastically restricted transcription and replication of the HSV-1 genome. Virology 192, 687–691.

SPIVACK, J. G. and FRASER, N. W. (1987). Detection of herpes simplex virus type 1 transcripts during latent infection in mice. J. Virol. 61, 3841–3847.

STEINER, I., SPIVACK, J. G., DESHMANE, S. L., ACE, C. I., PRESTON, C. M. and FRASER, N. W. (1990). A herpes simplex virus type 1 mutant containing a non-transinducing Vmw65 protein establishes latent infection in vivo in the absence of viral replication and reactivates efficiently from explanted trigeminal ganglia. J. Virol. 64, 1630–1638.

STERN, S., TANAKA, M. and HERR, W. (1989). The oct-1 homeodomain directs formation of a multiprotein-DNA complex with the HSV transactivator VP16. Nature 341, 624–630.

STEVENS, J. G. (1989). Human herpesviruses: a consideration of the latent state. Microbiological Rev. 53, 318–332.

STEVENS, J. G. and COOK, M. L. (1971). Latent herpes simplex virus in spinal ganglia of mice. Science 173, 843–845.

STEVENS, J. G., WAGNER, E. K., DEVI-RAO, G. B., COOK. M. L. and FELDMAN, L. (1987). RNA complementary to a herpesvirus alpha gene mRNA is predominant in latently infected neurons. Science 235, 1056–1059.

STINSKI, M. F. and ROEHR, T. J. (1985). Activation of the major immediate early gene of human cytomegalovirus by cis-acting elements in the promoter-regulatory sequence and by virus-specific trans-acting components. J. Virol. 55, 431–441.

STOW, N. D. and STOW, E. C. (1986). Isolation and characterisation of a herpes simplex virus type 1 mutant containing a deletion within the gene encoding the immediate early polypeptide Vmw110. J. Gen. Virol. 67, 2571–2585.

TRIEZENBERG, S. J., KINGSBURY, R. C. and McKNIGHT, S. L. (1988). Functional dissection of VP16, the trans-activator of herpes simplex virus immediate early gene expression. Genes Dev. 2, 718–729.

VALYI-NAGY, T., DESHMANE, S. L., SPIVACK, J. G., STEINER, I., ACE, C. I., PRESTON, C. M. and FRASER, N. W. (1991). Investigation of herpes simplex virus type 1 (HSV-1) gene expression and DNA synthesis during the establishment of latent infection by an HSV-1 mutant, in 1814, that does not replicate in mouse trigeminal ganglia. J. Gen. Virol. 72, 641–649.

WILSON, A. C., LAMARCO, K., PETERSON, M. G. and HERR, W. (1993). The VP16 accessory protein HCF is a family of polypeptides processed from a large precursor protein. Cell 74, 115–125.

ZWAAGSTRA, J. C., GHIASI, H., SLANINA, S. M., NESBURN, A. B., WHEATLEY, S. C., LILLYCROP, K., WOOD, J., LATCHMAN, D. S., PATEL, K. and WECHSLET, S. L. (1990). Activity of herpes simplex virus type 1 latency-associated transcript (LAT) promoter in neoron-derived cells: evidence for neuron specificity and for a large LAT transcript. J. Virol. 64, 5019–5028.

What is claimed is:

1. A mutant recombinant herpes simplex virus (HSV) viral vector genome comprising:
   (i) a mutation in a gene encoding a Vmw65 protein, the mutation being selected from the group consisting of:
      a transition or transversion alteration of 1–72 base pairs,
      an insertion of 3–72 base pairs, and
      a deletion of 3–72 base pairs,
      said mutation being at a position within said gene encoding an amino acid between amino acids 289 and 480 of the protein, wherein said mutant genome encodes a mutant Vmw65 protein lacking the ability to transinduce HSV-1 immediate early gene expression, whereby in vivo replication of the viral vector is prevented, wherein the ability of a virion produced from the viral vector genome to assemble is retained; and
   (ii) an expressable heterologous gene inserted into a region of the HSV genome which is non-essential for culture of the virus in vitro, the heterologous gene being under the control of an immediate early 1 (IE1) gene enhancer of cytomegalovirus (CMV), wherein said heterologous gene is expressed during latency of said virus;

wherein said mutation is a 12 base pair insertion at a in 1814 mutation site at a position within the Vmw65 gene encoding amino acid 379.

2. A recombinant HSV genome according to claim 1 wherein the CMV gene enhancer is the human CMV enhancer.

3. A recombinant HSV genome according to claim 1 wherein the CMV gene enhancer contains sequence variations such that the enhancer properties are not affected.

4. A recombinant HSV genome according to claim 1 wherein said HSV is HSV-1.

5. A recombinant HSV genome according to claim 1 wherein the expressable heterologous gene is selected from the group consisting of
   (a) human, rat or mouse tyro sine hydroxylase genes 1, 2 or 3;
   (b) human, rat or mouse nerve growth factor;
   (c) human, rat or mouse hypoxanthine-guanine phosphoribosyl transferase gene;
   (d) human beta-hexosaminidase alpha chain gene; and
   (e) human immunodeficiency virus (HIV) nef gene.

6. A recombinant HSV genome according to claim 1 wherein the heterologous gene is inserted in the coding sequence or in a flanking control region of an HSV-1 gene selected from the group of HSV-1 genes consisting of UL23; R11; RL2; UL2; UL3; UL4; UL10; UL11; UL13; UL16; UL20; UL24; UL40; UL41; UL43; UL44; UL45; UL46; UL47; UL50; UL55; UL56; US1; US2; US3; US4; US5; US7; US8; US9; US10; US11; US12; and the locus encoding latency associated transcripts.

7. An HSV mutant containing the genome of claim 1.

8. A method of treating disease comprising administering the recombination HSV genome of any one of claims 1–6 to a subject in need of such therapy.

9. A method of vaccination comprising administering the recombinant HSV genome of any one of claims 1–6 to a subject in need of vaccination.

10. A pharmaceutical composition comprising the recombinant HSV genome of any one of claims 1–6 in admixture with a pharmaceutically acceptable carrier.

* * * * *

UNITED STATES PATENT AND TRADEMARK OFFICE
CERTIFICATE OF CORRECTION

PATENT NO. : 6,613,892 B2  Page 1 of 1
DATED : September 2, 2003
INVENTOR(S) : Preston et al.

It is certified that error appears in the above-identified patent and that said Letters Patent is hereby corrected as shown below:

Title page,
Item [73], Assignee, "BTG International Inc." should read -- BTG International Limited --.

Column 17,
Line 20, "tyro sine" should read -- tyrosine --.

Column 18,
Line 7, "R11" should read -- RL1 --.

Signed and Sealed this

Sixth Day of January, 2004

JAMES E. ROGAN
*Director of the United States Patent and Trademark Office*